United States Patent [19]

Kurth

[11] Patent Number: 4,957,105
[45] Date of Patent: * Sep. 18, 1990

[54] FEMORAL COMPRESSION DEVICE FOR POST-CATHETERIZATION HEMOSTASIS

[76] Inventor: Paul A. Kurth, 1423 Brett Pl., Apt. 201, San Pedro, Calif. 90732

[*] Notice: The portion of the term of this patent subsequent to May 16, 2006 has been disclaimed.

[21] Appl. No.: 253,188

[22] Filed: Oct. 4, 1988

[51] Int. Cl.⁵ .............................................. A61F 5/24
[52] U.S. Cl. .............................. 128/96.1; 128/107.1; 128/DIG. 15; 606/203
[58] Field of Search ...................... 128/95.1, 96.1, 327, 128/100.1, 101.1, 106.1, 107.1, DIG. 15, 98.1, 99.1, 876

[56] References Cited

U.S. PATENT DOCUMENTS

| | | | |
|---|---|---|---|
| 1,399,386 | 12/1921 | Husar | 128/96.1 |
| 1,601,117 | 9/1926 | Hampton | 128/96.1 |
| 1,789,365 | 1/1931 | Hansen | 128/96.1 |
| 1,916,298 | 7/1933 | Brohman | 128/96.1 |
| 1,918,022 | 7/1933 | Drey | 128/96.1 |
| 1,992,397 | 2/1935 | Rowley | 128/96.1 |
| 2,449,641 | 9/1948 | Cidissen | 128/96.1 |
| 2,522,056 | 9/1950 | O'Brien | 128/96.1 |
| 3,021,838 | 2/1962 | Fine | 128/96.1 |
| 3,097,641 | 7/1963 | Nelkin | 128/96.1 |
| 3,308,813 | 3/1967 | Loeffel | 128/96.1 |
| 3,577,986 | 5/1971 | Regent | 128/96.1 |
| 3,754,549 | 8/1973 | Nelkin | 128/106.1 |
| 4,059,103 | 11/1977 | Glaser | 128/96.1 |
| 4,351,325 | 9/1982 | Walker | 128/96.1 |
| 4,416,272 | 11/1983 | Nelkin | 128/95.1 |
| 4,829,994 | 5/1989 | Kurth | 128/327 |

Primary Examiner—Robert A. Hafer
Assistant Examiner—Michael A. Brown

[57] ABSTRACT

An improved femoral arterial or venous compressive device includes a flexible pelvic apron positioned over the femoral vessels within the human pelvis. The pelvic apron is placed in position by means of a hip strap. The hip straps are led from the pelvic apron upwardly over the hip points, around the small of the back and down over the opposing hip point back to the pelvic apron. The pelvic apron thus hangs from the hip points of the pelvis much like an apron. A shaped mass or pellet is attached to the under side of the pelvic apron over the incision site of the femoral vessel. An elastically extensible groin strap is then attached to the pelvic apron in the proximity of the shaped mass and drawn tightly through the groin, around the back of the leg, under the buttocks and back upwardly to the pelvic apron in the proximity of the shaped mass. As a result, the tensile force is applied by the groin strap across the pelvic apron up to the hip point and also around the leg. The shaped mass is forced by the tourniquet action of the groin strap and pelvic apron in combination inwardly into the pelvis, thereby compressing the underlying femoral vessel and thus assisting in stanching any blood flow or fluid leakage.

21 Claims, 7 Drawing Sheets

FEMORAL COMPRESSION DEVICE FOR POST-CATHETERIZATION HEMOSTASIS

This invention is a continuation-in-part of Ser. No. 054,751, now U.S. Pat. No. 4,829,994.

BACKGROUND OF THE INVENTION

1. Field of the Invention

The invention relates to the field of medical sciences and in particular to devices used to facilitate femoral vascular stanching.

2. Description of the Prior Art

During cardiac catheterization and angiography, it is necessary to obtain access to the heart and other major body arteries and veins in order to visualize them with radioopaque materials. One of the preferred sites for such major vascular access is through the major femoral arteries and veins in the groin. The typical prior art procedure is to insert appropriate tubing into the femoral vessels through a small incision in the groin. The tube is later removed leaving a perforation in the femoral artery and/or vein. Normal blood clotting is utilized to render the repaired incision and vascular perforation blood-tight. Manual pressure is applied to the incision site for at least twenty minutes following removal of the tube from the artery or vein to allow for a clot of strength sufficient to withstand the arterial pressure of 120-180 mm Hg. Normally, manual pressure by trained medical personnel is sufficient to successfully clot the femoral arterial or venous perforation site and stanch the blood flow. However, despite this twenty minute time period the clot is soft and can be easily disrupted. Therefore, for some period of time thereafter it is advantageous to maintain a compressive force on the femoral puncture site to insure that it remains stanched.

The typical prior art procedure is to manufacture a thick pad of gauze which is placed over the site and taped securely to the patient's hip and groin in order to secure it in place and to maintain some compressive force over the incision site. The compressive force is generated and maintained by virtue of the bulk of the folded gauze pad pressed downwardly by the adhesive tape which is laid over the pad and which is attached on either side of the incision site to adjacent portions of the hip and groin.

Pursuant to the normal usage of such gauze and adhesive tape bandages, all contiguous areas of the incision site must be shaved and coated with an antiseptic and/or skin toughening agent. Approximately twenty-four hours later the bandages can be removed. However, a considerable amount of the body area in the area of the hip and groin is taped so that removal of the bandages is often an unpleasant and uncomfortable experience for the patient. Often some abrasion or skin tearing results and at the very least, there is some infliction of sharp temporary pain since the body area has been traumatized and is tender. Further, in many cases, patients may develop an allergic reaction to the adhesive or antiseptic applied to the body causing further tenderness and pain upon removal of the tape.

Further, if in the event that movement by the patient causes the blood clot to be damaged or dislodged, it may be necessary to reapply manual pressure and apply a new compression pad to the patient. In such a case, the old bandage must be quickly removed and the new bandage applied with the result that the patient may be subjected to the pain and discomfort of bandaging and unbandaging several times during the initial convalescence.

To avoid each of these drawbacks, the prior art has devised a groin compression device known as the Colapinto compression device, named after its creator in Canada. The Colapinto compression device is manufactured and sold under that name by Cook of Bloomington, Ind.

FIG. 1 is a frontal view of a patient bearing the prior art Colapinto device, generally denoted by reference numeral 10. FIG. 2 is a side view of the patient wearing the Colapinto device of FIG. 1. Briefly, the Colapinto device 10 includes a groin pad 12 which has a bi-lobed shape. A waist strap 14 is sewn at end 16 to groin pad 12 and wraps around the lower hips below the hip points, across the upper part of the buttocks and around the buttocks to the other side of groin pad 12 where strap 14 is attached at end 18 by means of a Velcro attachment provided to end 18 of strap 14 and the corresponding proximate portion of groin pad 12. Sewn to the lower center portion of groin pad 12 are two stabilizing straps 20 which are drawn between the legs and around the lower portion of each buttock and attached at end 22 to a Velcro fastener on strap 14 to the middle of the side of the hip as depicted in FIG. 2 below the hip point. The purpose and function of straps 20 are to provide only stabilization to groin pad 12 and they do not add in any material way to the compressive force applied by groin pad 12 to the underlying femoral arterial or venous incision site.

Shown in dotted outline in the left groin region under groin pad 12 in FIG. 1 is a styrofoam pellet in the shape of a sector of a sphere with a flattened pole. The diameter or cord of the sector is approximately 2⅞" with the thickness of the pellet from the flattened pole face to the base defined by the section is approximately one inch. Pellet 24 therefore is roughly hemispherical with a flattened pole face of approximately an inch across and serves to replace the equivalent amount of folded gauze to define the pressure point against the femoral arterial or venous incision.

Two material characteristics of the Colapinto compression device should be immediately noted. Firstly, the compressive force applied to pellet 24 by device 10 is substantially if not entirely created by virtue of the tension of waist strap 14. Pellet 24 is disposed on the relatively flattened front portion of the groin and the amount of downward compressive force which can be developed on pellet 24 by virtue of the tension of waist strap 14 is significantly limited.

Secondly, the Colapinto compression device can be used only either on the left or on the right femoral arterial site. For example, in the depiction of FIG. 1, if application to the left femoral arterial site was desired, pellet 24, which is attached by means of a Velcro fastening device to the back of groin pad 12, can be shifted to the left side of groin pad 12 and the entire groin pad similarly shifted to the left to position pellet 24 over the arterial site. The size and extent of groin pad 12 of the Colapinto device is not sufficient to allow simultaneous application to both left and right femoral arterial sites. In any case, it is unlikely that sufficient compressive force could be developed if two pellets were positioned underneath groin pad 12.

Therefore, what is needed is a compression device which overcomes each of the defects of the prior art and in particular which can apply a large and adjustable compression force to either the left or the right femoral vascular sites, or to both.

BRIEF SUMMARY OF THE INVENTION

The invention is an apparatus for applying pressure to a femoral vessel within the groin in the abdomen of a human body comprising a pellet for applying a directed force to the femoral vessel of the human body, a pelvic apron and a groin strap. The pelvic apron positions the pellet over the femoral vessel in one leg. The pellet is attached to the pelvic apron. The pelvic apron encircles the abdomen, extends downwardly toward the groin and completes encirclement of the abdomen at the groin. The groin strap applies a compressive force to the pellet thereby tending to compress the femoral vessel, so that a substantial inward force is adjustably applied to the femoral vessel and blood flow therefrom is stanched. The groin strap has a first and second end. The first end attaches to the pelvic apron. The groin strap extends over the point of attachment of the pellet to the pelvic apron toward the groin, around and behind the one leg. The second end of the groin strap attaches to the pelvic apron in overlapping proximity to the point of attachment of the pellet to include the pellet within the encirclement of the groin strap. The groin strap encircles the upper portion of the one leg and completes the encirclement at the groin where the apron completes encirclement of the abdomen. The groin strap and pelvic apron form in combination a figure of eight with the intersection of the figure of eight at the point of attachment of the pellet at the groin.

The pelvic apron comprises a flexible pelvic apron and a flexible hip strap having two ends. Each end attaches to the pelvic apron. The hip strap for positioning the pelvic apron on the human body.

The human body is characterized by having hip points defined by pelvic bones and the hip strap is connected to the pelvic apron over one of the hip points and extends from the hip point toward the groin in a vertically oriented direction more nearly parallel to the length of the human body than not.

The flexible pelvic apron is substantially non-extensible and the hip strap is elastically extensible. The groin strap is an elastically extensible strap having two ends. One end of the groin strap is attached to the pelvic apron in the proximity of the pellet. The groin strap is led through the groin of the human body around the corresponding leg of the human body and is attached to the pelvic apron in the proximity of the pellet.

The groin strap is separable from the apparatus, has a first and second end and is temporarily and adjustably attached at the first end of the groin strap to the pelvic apron. The groin strap is temporarily and adjustably attached at its second end to its own first end. Temporary and adjustable attachment of the first end of the groin strap to the pelvic apron and to its own second end is in the proximity of the pellet.

The pelvic apron comprises a flexible pelvic apron and a flexible hip strap having two ends. Each end is attached to the pelvic apron, the hip strap positions the pelvic apron on the human body. The hip strap is oriented relative to the pelvic apron so that the hip strap extends generally vertically across the abdomen to the groin.

The pelvic apron is comprised of a basal portion and at least one inclined portion. The inclined portion has a linear extent lying in a predetermined direction when the pelvic apron is disposed on the human body, the predetermined direction is directed to the hip point. The hip strap extends in a colinear direction with the predetermined direction to wrap around the hip point. The hip strap continues across the back of the human body and over the opposing hip point to be reattached to the pelvic apron. The groin strap is attached to the pelvic apron and lies in a colinear direction with the predetermined direction.

The groin strap is adjustable to provide variable tension along the groin strap and thus downward compression of the pellet toward the femoral vessel.

The invention is also characterized as a compression device for use as a femoral vascular clotting appartus for application to a human pelvis including a pair of opposing hip points, a groin, corresponding legs and corresponding femoral vessels extending through the pelvis into each of the legs. The device comprises a shaped mass having a first and second surface. Force applied to the first surface is transmitted through the mass to the second surface. The second surface is arranged and configured for placement in the proximity of the femoral vessel to apply compressive force to the femoral vessel when the mass is urged into the pelvis against the femoral vessel.

A pelvic apron securely positions the shaped mass on the human pelvis. The shaped mass is attachable to the pelvic apron at a predetermined range of locations between the pelvic apron and the human pelvis to position the mass proximate to the femoral vessel. The pelvic apron covers at least a frontal portion of the human pelvis. The pelvic apron encircles the human pelvis and completes encirclement of the human pelvis at the groin.

A groin strap is adjustably coupled to the pelvic apron for urging the shaped mass downwardly against the femoral vessel. The groin strap is attached to the pelvic apron and extends over the point of attachment of the pellet to the pelvic apron toward the groin, around and behind the one leg and attaches to the pelvic apron in overlapping proximity to the point of attachment of the shaped mass to include the shaped mass within the encirclement of the groin strap. The groin strap completes encirclement of the one leg at the groin where the pelvic apron completes encirclement of the human pelvis to form in combination with the pelvic apron a figure of eight entwined about the human pelvis and one leg. The shaped mass is attachable in the vicinity of the crossing of the figure of eight form.

As a result, the shaped mass is positioned by the pelvic apron and the compressive force is transmitted to the first surface of the shaped mass by tension applied by the groin strap to the pelvic apron.

The pelvic apron is positionally fixed with respect to one of the hip points and the groin strap applies a tensile force across the pelvic apron to the hip point and through the groin wherein an inwardly compressive force is applied to the first surface of the shaped mass. extent lying in a predetermined, generally vertical direction when the pelvic apron is disposed on the human body. The predetermined generally vertical direction is directed to the hip point and in line with the direction of extension of the groin strap over the pellet. The hip strap extends in a colinear direction with the predetermined generally vertical direction to wrap around the hip point. The hip strap continues across the back of the human body and over the opposing hip point to be reattached to the pelvic apron. The groin strap is attached to the pelvic apron and lies in a colinear direction with the predetermined generally vertical direction.

The invention is also a method for applying a compressive force to a femoral vessel within a human pelvis. The pelvis has two opposing hip points, a groin, and one leg extending from the groin. The method comprises the steps of stabilizing a shaped mass in position over a selected one of the femoral vessels in the human pelvis. The shaped mass is stabilized relative to at least one of the hip points. A downward compressive force is applied through the groin by means of a pelvic apron and a groin strap coupled to the shaped mass. The pelvic apron encircles the human pelvis and the groin strap encircles one leg. The compressive force is directed through the groin to the posterior portion of the human pelvis. The inward compressive force is generated by a posterior and upward pull by the pelvic apron in combination with a posterior and downward pull by the groin strap, so that the inward compressive force is applied to the shaped mass and ultimately to the underlying femoral vessel.

In the step of stabilizing the shaped mass in position, the shaped mass is positioned over the femoral vessel by attachment to a pelvic apron. The pelvic apron is positioned in turn over the human pelvis by means of a hip strap. The hip strap encircles the human pelvis and lies over the opposing hip points.

The invention can still further be characterized as an apparatus for applying inward pressure to a puncture site in the inguinal region of a human body to stanch blood flow comprising a pellet for concentrating pressure on the puncture site of the human body. A pelvic apron positions the pellet over the puncture site. The pellet is attached to the pelvic apron. A separable and adjustable groin strap i connected to the pelvic apron to apply a compressive force to the pellet, so that a substantial inward force is adjustably applied to the puncture site and blood flow therefrom is stanched. The groin strap extends over the point of attachment of the pellet to the pelvic apron toward the groin, around and behind the one leg and attaching to the pelvic apron in the overlapping proximity of the point of attachment thereto of the pellet to include the pellet within the encirclement of the groin strap. The pelvic apron and groin strap are thus connected with each other to topologically form a figure-of-eight shape having two loops and a crossing point between the two loops. One loop of the figure-of-eight encircles the trunk of the human body. The other loop of the figure-of-eight shape encircles a leg of the human body. The crossing point of the figure-of-eight is positioned substantially over the puncture site a portion of one loop. The crossing point and the contiguous portion of the opposing loop of the figure-of-eight form a generally straight and generally vertical segment over the pellet when the apparatus is disposed onto the human body.

The invention can also be described as a hemostatic device for stanching blood flow at an entry at a femoral site in an abdomen. The abdomen is characterized by a hip point, groin and thigh. The device comprises a first element for creating inward pressure over a hip arc extending from the hip point to the groin, and a second element for creating inward pressure in an oblique plane of the thigh. The first and second element both simultaneously create the inward force at the femoral site.

The invention can similarly be characterized as a method of applying a hemostatic device to staunch blood flow at an entry at a femoral site in an abdomen. The abdomen is characterized by a hip point, groin and thigh. The method comprising the steps of applying inward pressure over a hip arc extending from the hip point to the groin, and simultaneously applying inward pressure in an oblique plane of the thigh. Both steps of applying inward pressure apply the pressure at the femoral site.

The invention and its various embodiments are better visualized by now turning to the following drawings wherein like elements are referenced by like numerals.

The invention and its various embodiments may be better understood by now turning to the following detailed description.

DETAILED DESCRIPTION OF THE PREFERRED EMBODIMENTS

An improved femoral arterial and venous compressive device is comprised of a flexible pelvic apron positioned over the femoral arteries and veins within the human pelvis. The pelvic apron is placed in position by means of a hip strap. The hip straps are led from the pelvic apron upwardly over the hip points, around the small of the back and down over the opposing hip point back to the pelvic apron. The pelvic apron thus hangs from the hip points of the pelvis much like an apron. A shaped mass or pellet is attached to the under side of the pelvic apron over the puncture or incision site of the femoral vessels. An elastically extensible groin strap is then attached to the pelvic apron in the proximity of the shaped mass and drawn tightly through the groin, around the back of the leg, under the buttocks and back upwardly to the pelvic apron in the proximity of the shaped mass. As a result, the tensile force is applied by the groin strap across the pelvic apron up to the hip point and also around the leg. The shaped mass is forced by the tourniquet action of the groin strap and pelvic apron in combination inwardly into the pelvis, thereby compressing the underlying femoral artery and vein, and thus assisting in stanching any blood flow or fluid leakage.

Figure 3:
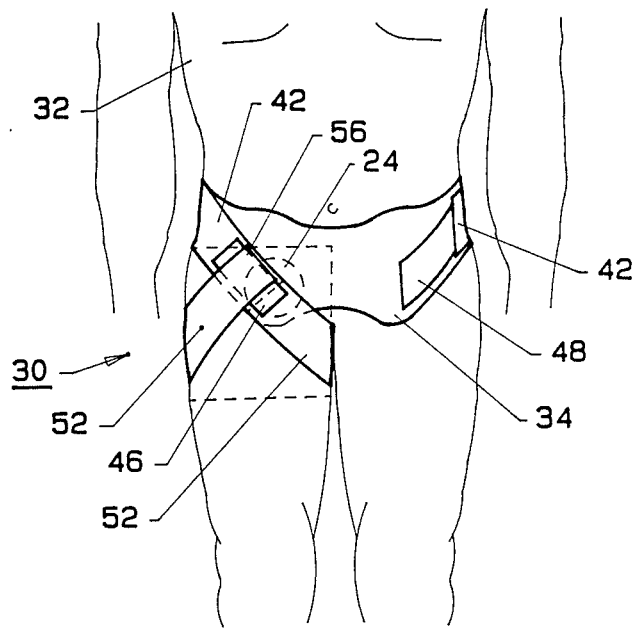
FIG. 3 is a front plan view of a compression device devised according to the invention.

The compression device of the invention, generally denoted by reference numeral 30, is depicted in the elevational plan view of FIG. 3 as fitted to a patient 32. The compression device 30, also to be known as the Kurth compression device, is comprised of a pelvic apron 34 made of a rubberized or substantially nonextensible fabric. As better depicted in plan view in FIG. 6, where Kurth compression device 30 is laid out flatly, pelvic apron 34 has a generally flattened V-shape comprised of a right upwardly extending leg 36, a bottom and mid-section 38 and a correspondingly left upwardly extending leg 40.

Figure 4:
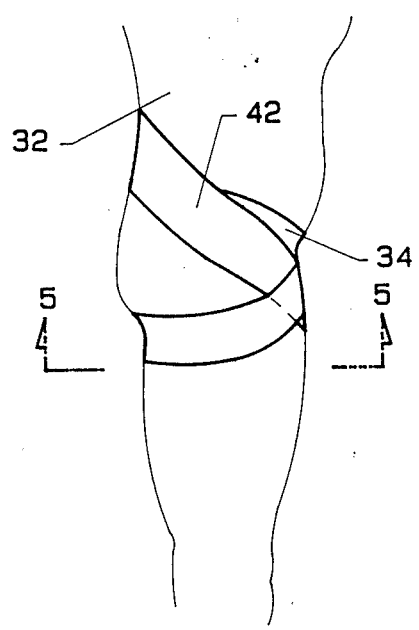
FIG. 4 is a side view of the compression device as applied to the patient as seen in FIG. 3.

Pelvic apron 34 of the Kurth compression device 30 differs from the Colapinto groin pad 12 in at least two significant respects. Firstly, pelvic apron 34 of Kurth compression device 30 is broader and spans the entire frontal pelvic region of patient 32. Thus, pelvic apron 34 is of sufficient size and extent such that a pellet, such as pellet 24 shown in FIG. 1, and shown in dotted outline in FIG. 3 and in a bottom perspective view in sectional FIG. 6, can be placed over either the left or right femoral site or both without shifting the position of pelvic apron 34 on patient 32. Secondly, upwardly extending portions 36 and 40 of pelvic apron 34 extend at a sharper angle to the horizontal than do the corresponding portions of the Colapinto device of FIG. 1 and 2. As seen in FIGS. 3 and 4, the angle of pelvic apron 34 is such that elastic strap 42 which lies along the line or direction of portion 40, for example, extends upwardly at an angle so that strap 42 lies directly over the patient's hip points or pelvic hip bones.

Figure 6:
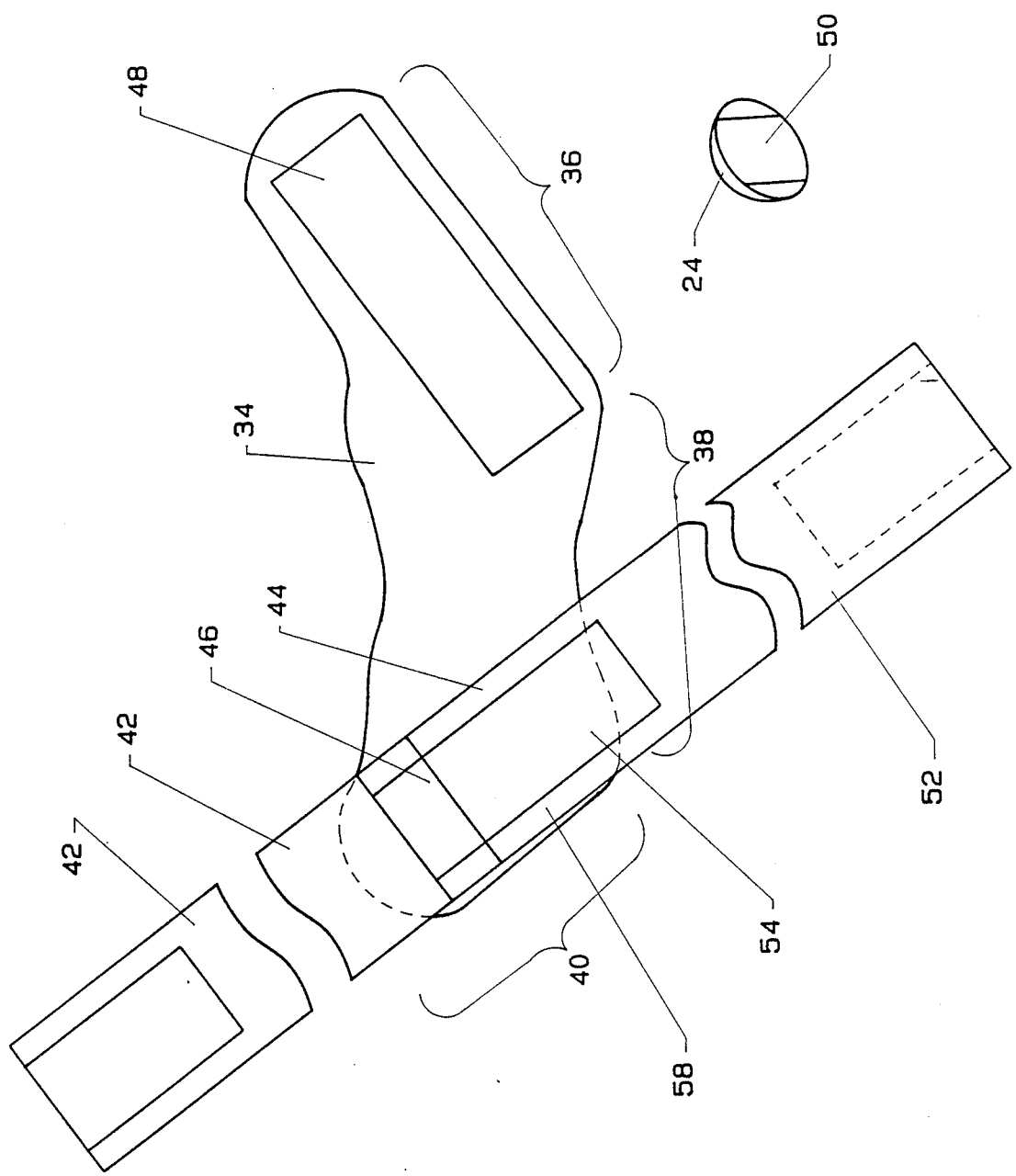
FIG. 6 is a front plan view of the compression device shown in broken away plan view as would be seen if the device were laid out flat.

As best depicted in FIG. 6, strap 42 is an elastic strap approximately three inches across as opposed to the Colapinto device which uses a two-inch strap. Strap 42 is sewn at one end to pelvic apron 34 and has a Velcro fastening patch 46 sewn to its outer surface overlying portion 40 of apron 34. A similar Velcro patch 48 is sewn to the opposing portion 36. In the illustrated embodiment, Velcro patches 46 and 48 act as hard hooks which are arranged and configured to engage a corresponding felt patch which acts as eyes of the Velcro fastener.

Strap 42 lies in a generally vertical direction when adjusted across the hip arc. In the present specification and claims, reference to a "generally vertical" strap 42 means that strap 42 is positioned on the body to approximately make a 45-60 degree angle with respect to a horizontal line, which is perpendicular to length or spinal direction of the body. Unlike prior art devices, the device of the invention incorporates and element for creating an inward force on the incision site, which element, i.e. strap 42, is thus characterized by a large vertical component by reason of its generally vertical orientation within the device when the device is applied to the abdomen.

As shown in side view in FIG. 4, strap 42 is drawn upwardly over the hip bone and across the lower back of patient 32 and attaches to the upper portion of Velcro patch 48 as depicted in FIG. 3. Thus, on the inside surface of strap 42 is a soft felt Velcro strip of eyes (not shown) which can be placed against the hard Velcro hooks on patch 48. The angle of strap 42 as it attaches to patch 48 is generally parallel to the angle of portion 36 of pelvic apron 34 and also rides over the adjacent hip point.

Pellet 24, which is shown in the illustrated embodiment of FIG. 3, is attached to pelvic apron 34 over the right femoral vascular site and prior to the attachment of groin elastic strap 52 has at this time very little compressive force applied to it. Pellet 34 is maintained in place and connected to the under side of pelvic apron 34 by a Velcro attachment which is sewn to the appropriate position on the under side of pelvic apron 34 (not shown). An opposing and corresponding Velcro attachment patch 50 is glued or otherwise attached to the bottom of plastic or styrofoam pellet 34 as shown in perspective view in FIG. 6. Because of the spatial extent of both patch 50, pellet 24 and the corresponding patch on the bottom side of pelvic apron 34, the exact position of pellet 24 can be varied with a fair degree of latitude to position it directly over the incision site.

In any case, after pelvic apron 34 has been secured to the patient by means of hip strap 42, it is positioned on the under side of pelvic apron 34, which at this point would essentially hang loosely downward if the patient were to stand.

The Kurth compression device 30 further comprises a separate compression strap 52 which is an identical elastic strap approximately 22 inches long, as depicted in broken plan view in FIG. 6. Groin strap 52 is provided with a Velcro patch on its under side (not shown) which is laid against Velcro patch 46 sewn to pelvic apron 34. The opposing side of strap 52 is also provided with a Velcro patch 54, which in the illustrated embodiment is comprised of the hard Velcro hooks. Strap 52 is laid on and connected to pelvic apron 34 and the hip strap 42 in such a manner that it would lie approximately colinearly with the line of portion 40 of apron 34 and with strap 42, if they were laid out on a flat surface as shown in FIG. 6.

As shown in FIGS. 3 and 4, strap 52 is extended between the patient's legs, around the back of the leg, underneath the buttock, against the back of the leg and back to the attachment location on portionn 40 close to or actually overlapping pellet 24. Groin strap 52 thus has a sewn Velcro patch on its underside on end 56, which patch can be laid across and attached to Velcro patch 54 on the opposing end 58 of groin strap 52. Thus, one end of hip strap 42 and both ends of groin strap 52 join at the same general location on pelvic apron 34 above or in the close proximity of pellet 24.

As will be better understood by turning to the sectional view of FIG. 5, as described below, a nearly unlimited amount of compressive force can be applied to pellet 24 as a result of this configuration.

Groin strap 52 may be removed from the right side of pelvic apron 34 as shown in FIG. 3 and reattached in a similar manner to the left side. More specifically, strap 52 is placed and attached to its Velcro pad to Velcro patch 48 sewn into portion 36 of pelvic apron 34 and laid in a line of direction approximately colinear with the line of portion 36 and hip strap 42 which is connected to the opposing end of pad 48. Groin strap 52 is then drawn between the legs and again across the upper portion of the back leg underneath the buttock to reattach to its opposing end on top of pelvic apron 34 and patch 48. In such a case, pellet 24 would be moved to the left side of pelvic apron 34 or an additional pellet 24 would be inserted therein. Therefore, it is also possible that two such groin straps would be attached and included within the Kurth compression device 30.

Figure 5:
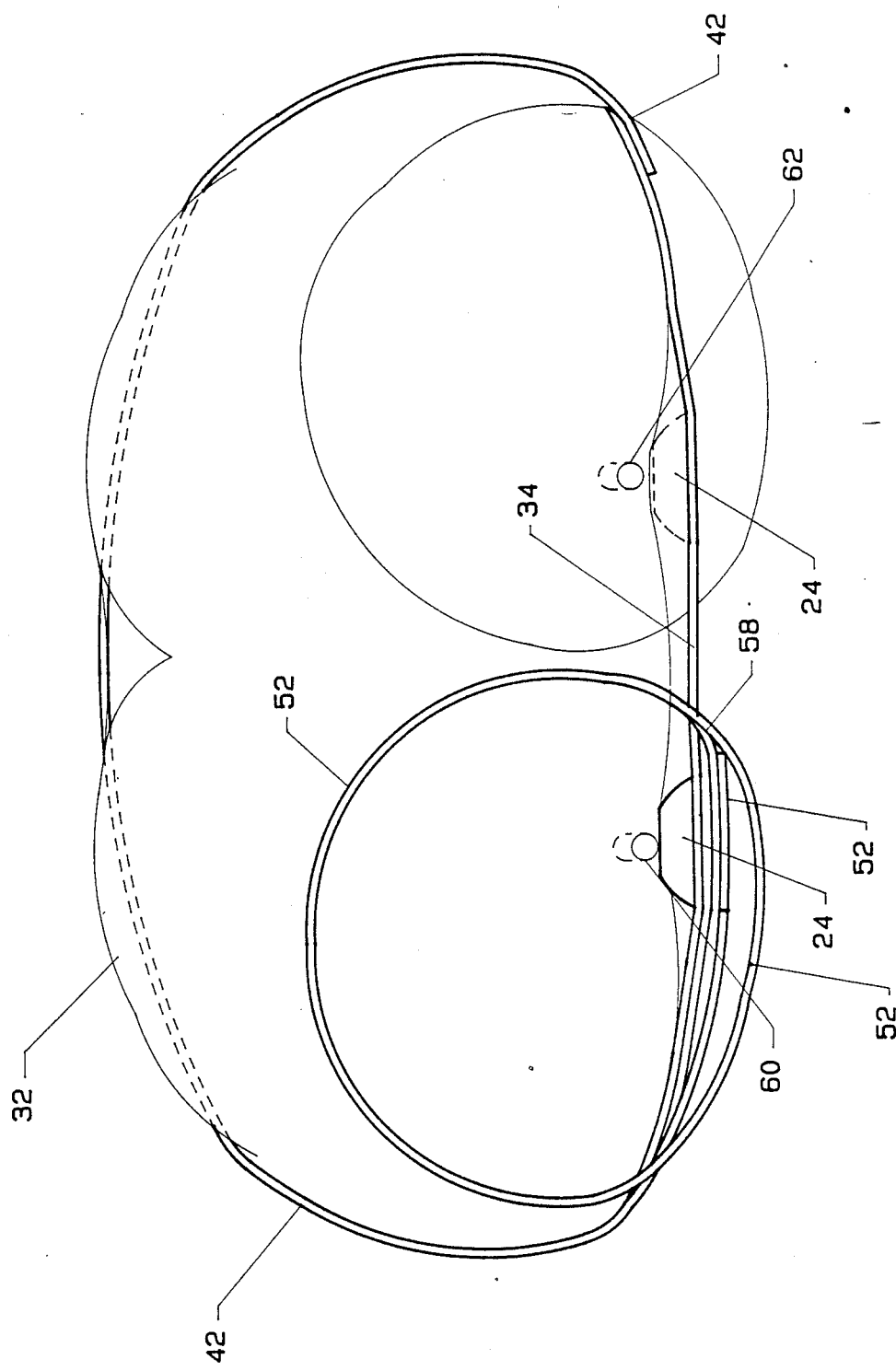
FIG. 5 is an elevational view of the compression device of the invention as would be seen through section lines 5—5 of FIG. 4.

Turn now to FIG. 5 wherein the mechanics of the Kurth compression device 30 may be better understood and depicted. FIG. 5 is an enlarged cross-sectional view of patient 32 as would be seen in a section through lines 5—5 of FIG. 4 looking upwardly. The left femoral artery is denoted by reference numeral 60. Pellet 24 is positioned on the groin immediately above artery 60 and held in place by means of pelvic apron 34. Groin strap 52 then attaches to pelvic apron 34 above pellet 24 and wraps around the leg back across pelvic apron 34 and attaches to the top of opposing end 58 of strap 52. The human body presents a complex shape and the interrelationship of stresses distributed throughout Kurth compression device 30 is similarly complex. It cannot be totally analytically understood with absolute quantified certainty how the physics of device 30 actually distributes tensile forces to result in certain compressive forces. However, it can be graphically seen in FIG. 5 that groin strap 52 may serve as a tourniquet which tightens on the groin where the leg attaches to the hip. It is also believed that a lever action may be achieved which is pivoted on the hip point and concentrated by the relatively sharp curvature of the groin at the femoral arterial site.

Figure 1:
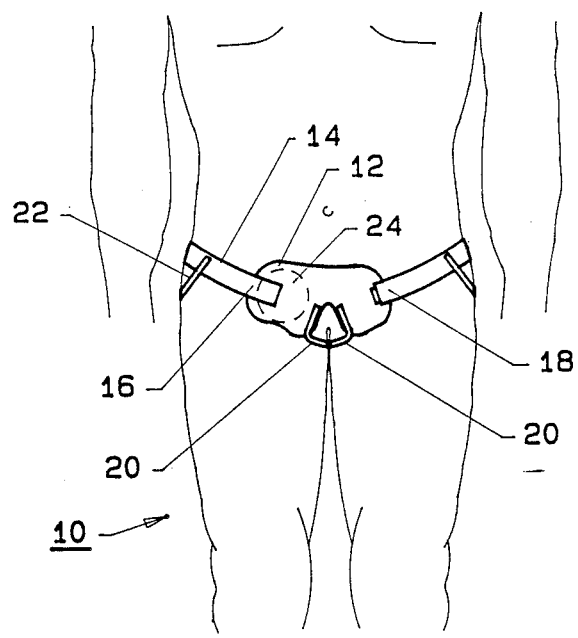
FIG. 1 is a front plan view of a prior art device shown as applied to a patient.
Figure 2:
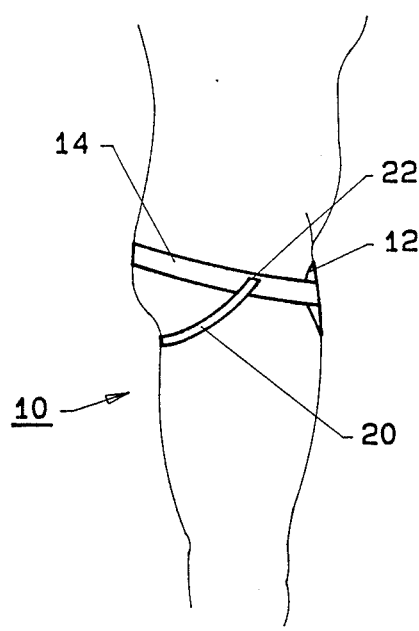
FIG. 2 is a side view of the prior art device depicted in FIG. 1.

As strap 52 is tightened according to its manual attachment as described above, the amount of compressive force applied to pellet 24 can be varied. The difference in the amount of compressive force which can be applied to pellet 24 by the Kurth compression device 30 as compared to the Colapinto compression device of FIGS. 1 and 2 is substantial and immediately noticeable by patient 32. The compressive force which can be applied by Kurth compression device 30 is sufficient, if desired, to totally close off artery 60. Lesser degrees of force from complete closure to virtually no compressive force can be applied by adjusting the tension on the strap 52.

The sectional view of FIG. 5 also illustrates the aspect of the invention wherein a second pellet 24 is placed over the right femoral artery 62. For the sake of clarity, no groin strap 52 is shown connected to pelvic apron 34 and therefore virtually no compressive force is applied to pellet 34 above femoral artery 62.

Distinctions between the present invention of the prior art can best be understood by considering one specific prior art device as shown in Nelkin, "Truss", U.S. Pat. No. 3,754,549 (1973). The Nelkin device is a hernial belt and is depicted diagrammatically in front elevational view in FIG. 7 as applied to the human abdomen. The Nelkin hernial belt, generally devoted by reference numeral 100, is comprised of a generally horizontal circumferential waistband 102 which is the primary, if not, the sole means for creating an inward force against a hernial pad 104. A groin strap 106 is integrally fixed or stitched to waistband 102 and extends from the or left side of belt 100 as seen in FIG. 7, down through the groin and upwardly over the back of the buttock to the back of waistband 102.

Figure 7:
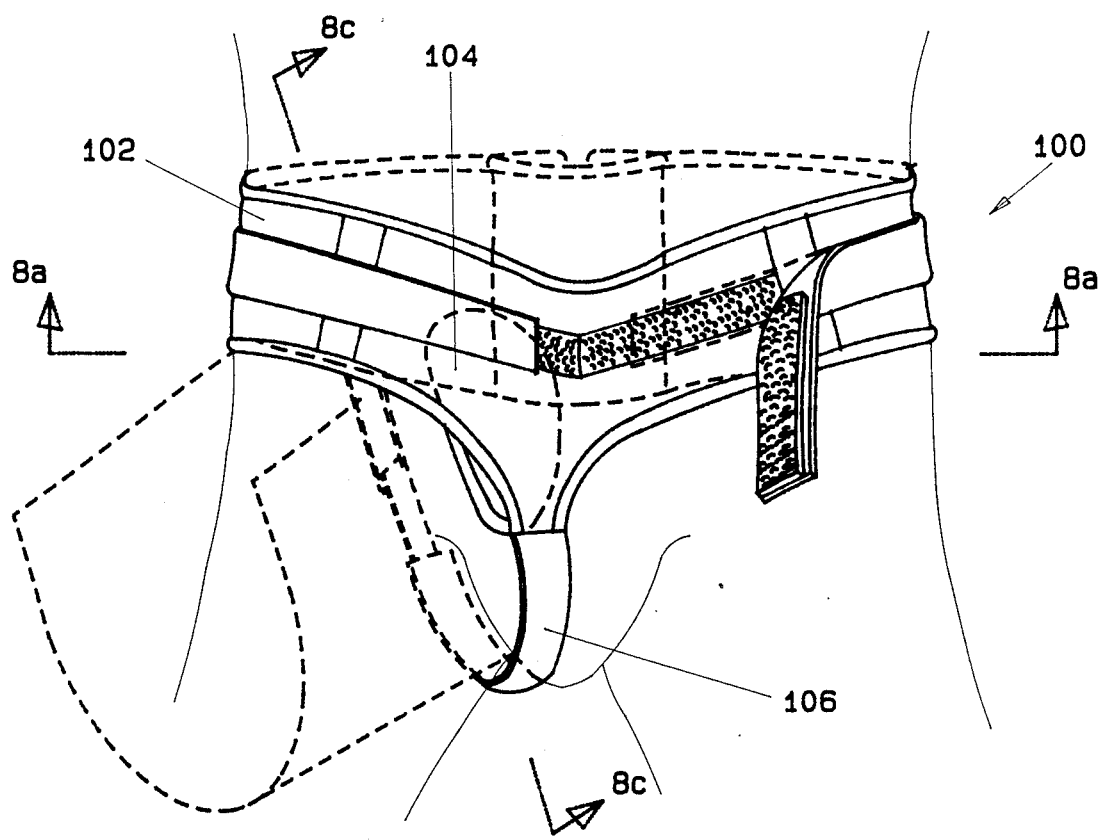
FIG. 7 is a diagrammatic front elevational view of a human pelvis fitted with a prior art device such as shown in Nelkin, U.S. Pat. No. 3,754,549 (1973).

Belt 100 as depicted in FIG. 7 is thus suitable for applying an inward pressure on a hernia on the right side of the abdomen. Pad 104 can be positioned symmetrically across the mid line of belt 100 to be applied to the left side of the abdomen. It is not necessary to provide or devise a belt with a groin strap 106 attached to the left side of belt 100 in order for belt 100 to be used for left sided hernias, because the function of groin strap 106 is primarily, if not solely, to prevent waistband 102 from riding up the abdomen as the wearer of the belt moves about.

Figure 8A:
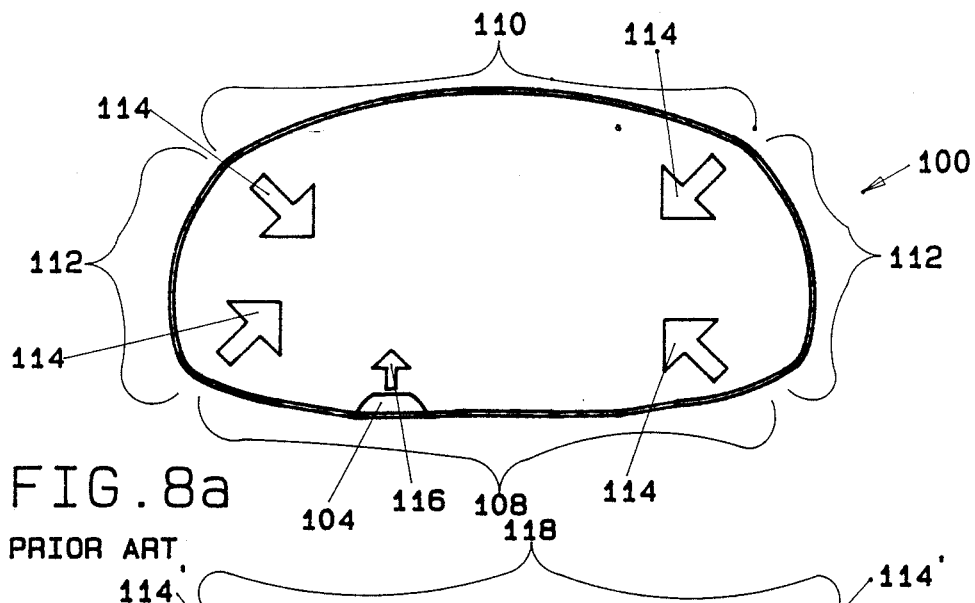
FIG. 8a is a diagrammatic cross-sectional view of the Nelkin device as seen through section lines 8a—8a in FIG. 7.
Figure 8B:
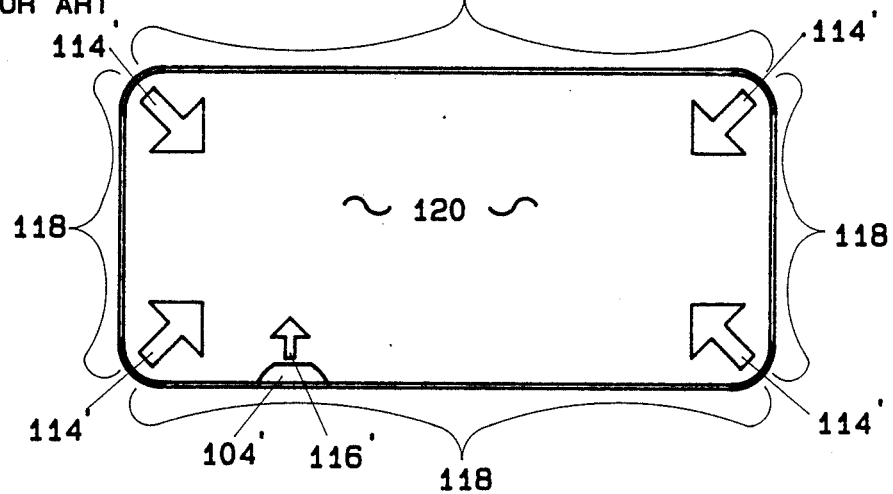
FIG. 8b is a geometric symbolization of the Nelkin device of FIG. 8a graphically depicting the distribution of inward forces which the prior device applies to the abdomen.
Figure 8C:
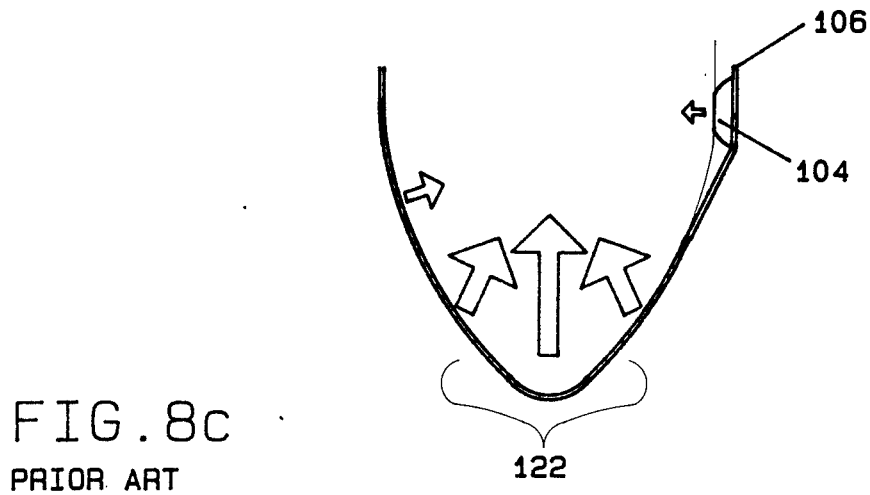
FIG. 8c is a cross-sectional view taken through the groin strap of the Nelkin belt as seen in section lines 8c—8c of FIG. 7, symbolically depicting the distribution of the inward forces on the body.

FIGS. 8a–8c diagrammatic illustrates the distribution of inward forces which are created by the Nelkin belt of FIG. 7. Turn first to FIG. 8a which is a diagrammatic depiction taken through the horizontal cross-section 8a—8a of FIG. 7 through the lower part of waistband 102 and horizontally across the abdomen. FIG. 8a graphically illustrates the fact that a horizontal cross-section through the abdomen is generally rectangular in shape. Those portions 108 and 110 of waistband 102 which extend across the front and rear of the adbomen respectively are relatively flat sections of waistband 102 while greater radii of curvatures of waistband 102 are experienced in side portions 112 of waistband 102.

As explained diagrammatically in connection with FIG. 8b below, the maximum inward forces which are exerted by waistband 102 of belt 100 at the portions of waistband 102 of highest radii of curvature, represented by arrows 114. A substantially smaller inward force 116 is developed at the flatter portions of 108 and 110 of waistband 102.

This principle is more graphically illustrated by the depiction of FIG. 8b which shows a belt 102' wrapped under tension around a solid rectangular block. The inward force developed along the flat sides 118 is quite small and in fact may be very nearly zero, if there is no extension of belt 102' away from the flat sides of block 120. Instead, the inward force developed by tensioned belt 102' into block 120 will occur at corners where there is a higher radius of curvature as depicted by arrows 114'. An inward force 116' is developed on pad 104' only to the extent that the surface of block 120 would push outwardly against pellet 104' and distort flat portion 118' of band 102. It can be intuitively appreciated that the magnitude of concentration of inward forces 114' are accentuated the shaper the corners of block 120.

FIG. 8c is a diagrammatic cross-sectional view taken through section lines 8c—8c of FIG. 7 following the contour or sectional line of groin strap 106 of Nelkin's hernial belt. As shown in the perspective view of the dotted projection of FIG. 7, the shape of the body section on which groin strap 106 lies is generally parabolic in nature. The sharpest angle of curvature appears at the bottom of the groin, namely along bottom strap portion 122. The more tension which is applied to groin strap 106, the greater is the upward force along portion 122 at the bottom of the groin. Pad 104 of Nelkin's hernial belt in fact occurs at a relatively flat portion of the body section, and therefore only a minimal inward force is applied, if at all, by groin strap 106 on pad 104. It is believed that the primary inward force on pad 104 is applied through waistband 102 as depicted in FIG. 8a. In fact, excessive tensioning of groin strap 106 is likely only to lead to uncomfortable pinching or binding in the bottom of the groin without any corresponding increase on the inward pressure applied on pad 104.

This is generally not a problem with the prior art Nelkin hernial belt because groin strap 106 is not intended to be utilized to any appreciable extent to create inward pressure on pad 104. Moreover, the amount of inward force which is required against a repaired hernia site is substantially less than is required for pressure cauterization of a femoral artery puncture site where vessel pressures of the order 100 mm Hg must be securely closed following cauterization.

Figure 9C:
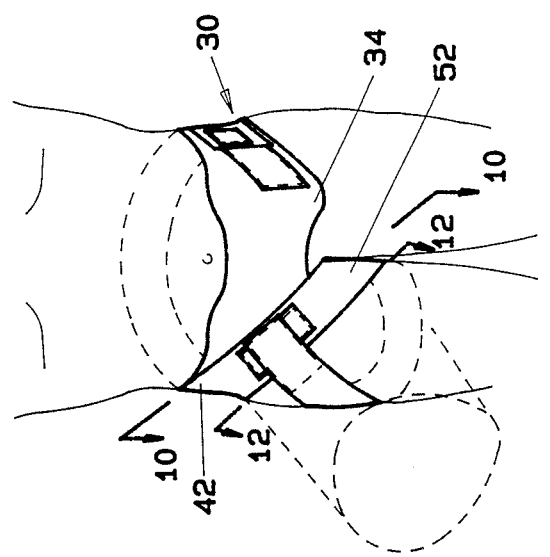
FIGS. 9a—9c are diagrammatic front elevation views depicting the invention and its application to the body.
Figure 9B:
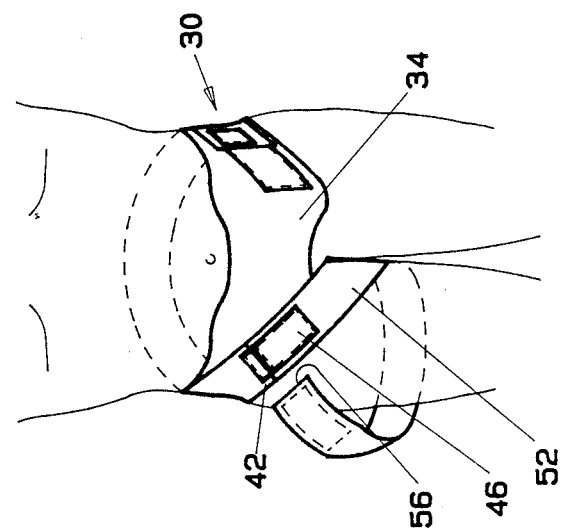
Figure 9A:
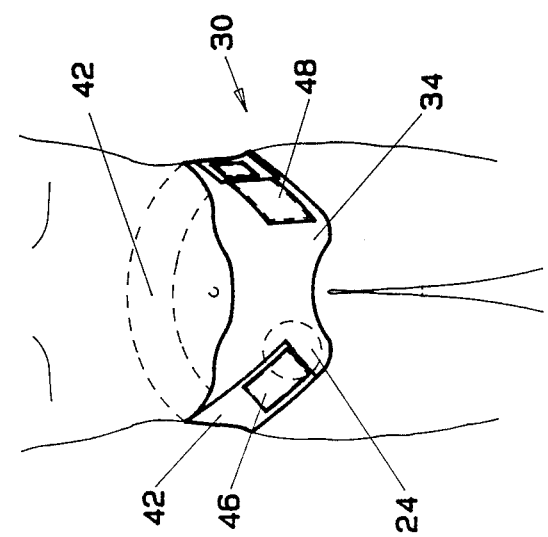
Figure 10:
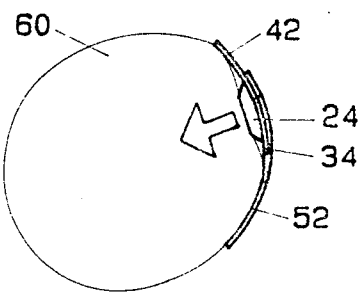
FIG. 10 is a diagrammatic sectional view of the hip arc portion of the invention as seen through section lines 10—10 of FIG. 9c.
Figure 11:
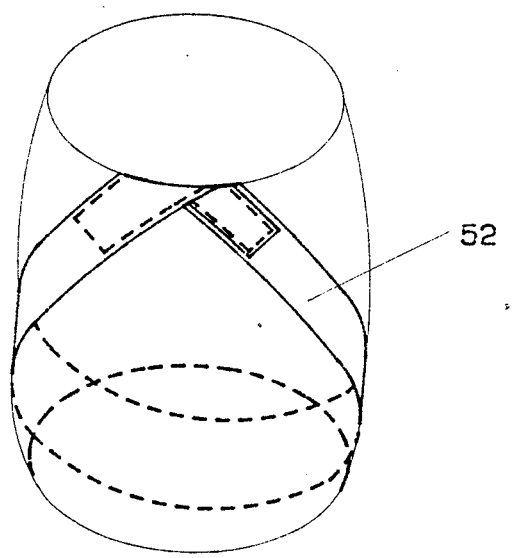
FIG. 11 is a diagrammatic perspective view of the leg strap portion of the invention taken from the dotted section depicted in FIG. 3 and illustrating the positioning of the leg strap around the barrel of the thigh.

Prior art devices and the forces which they provide on the abdomen now having been analyzed, turn to FIGS. 9-11 wherein the invention is correspondingly depicted. In FIG. 9a, the hemostatic/exclusive leverage device as previously described in connection with FIGS. 3-6 is shown in FIGS. 9a-9c as being applied to a human abdomen. The hemostatic compression device, generally devoted by reference numeral 30 is adjusted to the human body by first placing apron 34 across the front and lower portion of the abdomen followed by placing waistband strap 42 across the upper back of the abdomen as shown in dotted outline of FIG. 9a and in side view in FIG. 4. Waistband stap 42 is snugly secured about the patient's waist above the point of both hips so that pelvic apron 34 rests on the umbilicus. A light foam disc or pellet 24 is then placed inside apron 34 as shown in dotted outline in FIG. 9a. As previously described, Velcro patches are provided for this attachment. The surgical procedure is then carried out.

After the surgical procedure of cauterization has been completed, manual pressure is applied to the femoral puncture site and a sterile dressing is applied to the entry site. Pelvic apron 34 is pulled down with both hands to the public area and groin strap 52 is attached to Velcro patch 46 on outer surface of pelvic apron 34. In FIG. 9b groin strap 52 is applied directly over the puncture site, typically over pellet 24. Foam pellet 24 is positioned at this time directly over the dressing or entry site.

As shown in FIG. 9b, groin strap 52 is wrapped around the inner thigh, extends posteriorly below the buttock and continues around the outer thigh, terminating with an attachment directly over the puncture site. Again attachment is provided by Velcro patches. FIG. 9b illustrates the hemostatic device of the invention just prior to the attachment of end 56 back to patch 46.

The fully assembled or fitted hemostatic device is shown in FIG. 9c with the portion wrapped around the rear of the thigh depicted in dotted outline. Inward forces are applied to pellet 24 at the point of attachment of groin strap 52 to apron 34. This inward pressure is developed firstly by pressure from a hip arc extending in a somewhat vertical direction from the hip point at waistband strap 42, continuing across pellet 24 and terminating on the inner thigh with groin strap 52. The complete encirclement of the thigh by groin strap 52 provides a second source of inward pressure on pellet 24 by means of the completed tourniquet depicted in FIG. 9c and in greater detail in FIGS. 11 and 12.

First turn to consider the force developed on pellet 24 by virtue of inward force created across the hip arc. The section of the body, from hip point to the groin, is seen through section lines 10—10 in dotted perspective view in FIG. 9c and in cross-sectional view in FIG. 10. The curve of the body from the hip point to the inner thigh as seen in cross-sectional view of FIG. 10 is spanned by waist strap 42 beginning at the region of the hip point 60. Pellet 24 as described is attached to underside of apron 34 and the hip arc is completed by the upper portion of groin strap 52. A complete enclosure is not seen through the section of FIG. 10 since waist strap 42 turns at the plane of the section and is wrapped behind the back while groin strap 52 turns out of the section and is wrapped behind the thigh. Nevertheless, tension is maintained across the hip arc and inward force is exerted on pellet 24.

The upper portion of thigh and adjacent portions of the trunk generally form a barrel shape. The barrel of the thigh is depicted in dotted outline in FIG. 3 is shown in diagrammatic perspective view in FIG. 11. Groin strap 52 is shown as completely and encircling the barrel of the thigh and thereby providing a tourniquet through the section defined by the closed loop of groin strap 52.

Figure 12:
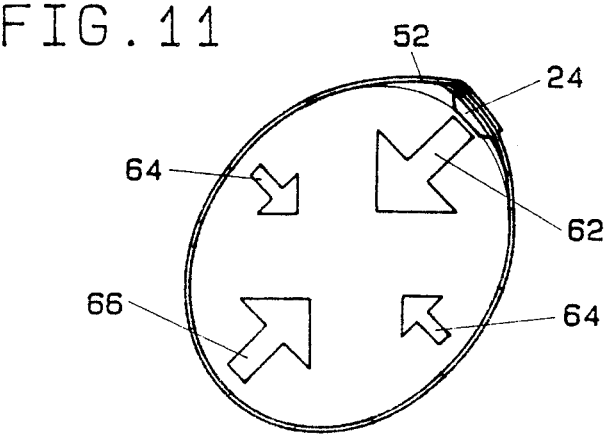
FIG. 12 is a cross-sectional view taken through the thigh strap of the invention and as seen through section 12—12 of FIG. 9c, which section is in an oblique plane through the thigh.

The plane of groin strap 52 is seen through the oblique section 12—12 through the barrel of the thigh and is depicted in cross-sectional view in FIG. 12. The barrel of thigh thus appears generally elliptical with pellet 24 placed near one of the foci of the ellipse and groin strap 52 completely encircling the oblique section of the thigh. In this case, not only does tensioning groin strap 52 result in tourniquet effect on the abdominal oblique section of FIG. 12, but a portion of groin strap 52 which has the highest radii of curvature tends to be in the vicinity of or at pellet 24, so that the maximum amount of inward force developed by groin strap 52 is applied directly to pellet 24. This maximal inward force is diagrammatically depicted by arrow 62 in FIG. 12 with substantially smaller inward force applied elsewhere along the section of FIG. 12 as diagrammatically depicted by arrows 64 and 66.

Therefore, in contrast to the prior art, where the groin provides as maximal inward pressure at the bottom of the groin, far removed from pad 104 as diagrammatically depicted in FIG. 8c, the present invention develops an inward force which tends to be maximized at the position of pellet 24 of groin strap 52. Increasing the tension on groin strap 52 also creates an inward pressure along the hip arc as depicted in FIG. 10 without the creation of a pressure point or an area of pinching or binding elsewhere within the hemostatic device.

FIGS. 9a-9c also illustrate a feature of the invention made possible by the fact that groin strap 52 is a separate element of the compression device. Firstly, adjustment is quickly and easily effected by means of the velcro patch attachments, and secondly, one size of device fits all patients regardless of their size or particular body figure. Even more importantly, the separability of groin strap 52 allows the device to be used either on a left or right side femoral site with equal ease and without the need for the supply of a left- or right-handed design as would be the case with Nelkin. Still further, the design is such that both left and right femoral sites can be simultaneously but separately adjusted and stanched with the addition of a second groin strap 52. Since very little inward pressure on pellet 24 is created by apron 34, apron 34 can be fitted as shown in FIG. 9a with the patient standing and before the surgical procedure. After the surgical procedure a supine patient can remain supine and the appropriate leg lifted slightly to allow the fitting of groin strap 52 at which time an much inward pressure as needed can be created on pellet 24 both on the hip arc as well as the oblique thigh plane by tensioning groin strap 52.

Many modifications and alterations may be made by those having ordinary skill in the art without departing from the spirit and scope of the invention. The illustrated embodiment has been set forth only for the purposes of example and should not be taken as limiting the invention which is defined by the following claims.

I claim:

1. An apparatus for applying pressure to a femoral vessel within the groin in the abdomen of a human body comprising:
   a pellet means for supplying a directed force to said femoral vessel of said human body;
   a pelvic apron means for positioning said pellet means over said femoral vessel in one leg, said pellet means attached to said pelvic apron means, said pelvic apron means encircling said abdomen, extending downwardly toward said groin and completing encirclement of said abdomen at said groin; and
   groin strap means for applying a compressive force to said pellet means tending to compress said femoral vessel, so that a substantial inward force is adjustably applied to said femoral vessel and blood flow therefrom is stanched, said groin strap means having a first and second end, said first end attached to said pelvic apron means, said groin strap means extending over said point of attachment of said pellet means to said pelvic apron means toward said groin, around and behind said one leg, said second end of said groin strap means attaching to said pelvic apron means in the overlapping proximity of said point of attachment thereto of said pellet means to include said pellet means within the encirclement of said groin strap means, said groin strap means encircling the upper portion of said one leg and completing said encirclement at said groin where said apron means completes encirclement of said abdomen, said groin strap means and pelvic apron means forming in combination a figure of eight with the intersection of said figure of eight at said point of attachment of said pellet means at said groin.

2. The apparatus of claim 1 wherein said pelvic apron means comprises a flexible pelvic apron and a flexible hip strap having two ends, each end attached to said pelvic apron, said hip strap for positioning said pelvic apron on said human body.

3. The apparatus of claim 2 wherein said human body is characterized by having hip points defined by pelvic bones and wherein said hip strap is connected to said pelvic apron over one of said hip points and extends from said hip point toward said groin in a vertically oriented direction more parallel to the length of said human body than not.

4. The apparatus of claim 2 wherein said flexible pelvic apron is substantially non-extensible and said hip strap is elastically extensible.

5. The apparatus of claim 1 wherein said groin strap means is an elastically extensible strap having two end, one end of said strap being attached to said pelvic apron means in the proximity of said pellet means, said groin strap being led through the groin of said human body around the corresponding leg of said human body and attached to said pelvic apron means in the proximity of said pellet means.

6. The apparatus of claim 1 wherein said groin strap is separable from said apparatus has a first and second end and is temporarily and adjustably attached at said first end of said groin strap to said pelvic apron means, and is temporarily and adjustably attached at said second end to said first end of said groin strap, temporary and adjustable attachment of said first end of said groin strap to said pelvic apron means and to its own second end being in the proximity of said pellet means.

7. The apparatus of claim 1 wherein said pelvic apron means comprises a flexible pelvic apron and a flexible hip strap having two ends, each end attached to said pelvic apron, said hip strap for positioning said pelvic apron on said human body, said hip strap being oriented relative to said pelvic apron so that said hip strap extends generally vertically across said abdomen to said groin.

8. The apparatus of claim 7 wherein said pelvic apron is comprised of a basal portion and at least one inclined portion, said inclined portion having a linear extent lying in a predetermined direction when said pelvic apron is disposed on said human body, said predetermined direction being directed to the hip point, said hip strap extending in a colinear direction with said predetermined direction to wrap around the hip point, said hip strap continuing across the back of said human body and over the opposing hip point to be reattached to said pelvic apron, said groin strap being attached to said pelvic apron and lying in a colinear direction with said predetermined direction.

9. The apparatus of claim 8 wherein said groin strap is adjustable to provide variable tension along said groin strap and thus inward compression of said pellet means toward the femoral vessel.

10. The apparatus of claim 1 wherein said pellet means is comprised of two separate and shaped masses attached to said pelvic apron means, each mass being shaped to transmit force applied to said mass to a predetermined area of said human body in contact with said mass.

11. A compression device for us as a femoral vascular clotting apparatus for application to a human pelvis including a pair of opposing hip points, a groin, corresponding legs and corresponding femoral vessels extending through said pelvis into each of said legs comprising:
   a shaped mass having a first and second surface, force applied to said first surface being transmitted through said mass to said second surface, said second surface arranged and configured for placement in the proximity of said femoral vessel to apply compressive force to said femoral vessel when said mass is urged into said pelvis against said femoral vessel;
   pelvic apron means for securely positioning said shaped mass on said human pelvis, said shaped mass being attachhable to said pelvic apron means at a predetermined range of locations between said pelvic apron means and said human pelvis to position said mass proximate to said femoral vessel, said pelvic apron means covering at least a frontal portion of said human pelvis, said pelvic apron means encircling said human pelvis and completing encirclement of said human pelvis at said groin;
   groin strap means adjustably coupled to said pelvic apron means for urging said shaped mass inwardly against said femoral vessel, said groin strap means attached to said pelvic apron means and extending over said point of attachment of said pellet means to said pelvic apron means toward said groin, around and behind said one leg and attaching to said pelvic apron means in the overlapping proximity of said point of attachment thereto of said shaped mass to include said shaped mass within the encirclement of said groin strap means, said groin strap means completing encirclement of said one leg at said groin where said pelvic apron means completes encirclement of said human pelvis to form in combination with said pelvic apron means a figure of eight entwined about said human pelvis and one leg, said shaped mass attachable in the vicinity of the crossing of said figure of eight form, whereby said shaped mass is positioned by said pelvic apron means and whereby said compressive force is transmitted to said first surface of said shaped mass by combination of tension applied by said groin strap means to said pelvic apron means.

12. The compression device of claim 11 wherein said pelvic apron means is positionally fixed with respect to one of said hip points and wherein said groin strap means applies a tensile force across said pelvic apron means to said hip point and through said groin wherein an inwardly compressive force is applied to said first surface of said shaped mass.

13. The compression device of claim 12 wherein said groin strap means is elastically extensible and wherein tensile force applied by said elastically extensible groin strap means is variably adjustable.

14. The compression device of claim 12 wherein said groin strap means is elastically extensible and wherein tensile force applied by said elastically extensible groin strap means is variably adjustable, and
    wherein said pelvic apron means is comprised of a substantially non-extensible pelvic apron and an elastically extensible hip strap means for binding said pelvic apron to said hip points of said pelvis wherein said pelvic means is comprised of a basal portion and at least one inclined portion, said inclined portion having a linear extent lying in a predetermined, generally vertical direction when said pelvic apron is disposed on said human body, said predetermined generally vertical direction being directed to the hip point and in line with said direction of extension of said groin strap means over said pellet means, said hip strap means extending in a colinear direction with said predetermined generally vertical direction to wrap around the hip point, said hip strap means continuing across the back of said human body and over the opposing hip point to be reattached to said pelvic apron, said groin strap being atttached to said pelvic apron and lying in a colinear direction with said predetermined generally vertical direction.

15. The compression device of claim 14 wherein said groin strap means has two ends, a first end connected to said pelvic apron means, said groin strap being led through said groin around said corresponding leg and said second opposing end of said groin strap being attached to said pelvic apron.

16. The compression device of claim 15 wherein said two ends of said groin strap are each connected to said pelvic apron in the proximity of said shaped mass.

17. A method for applying a compressive force to a femoral vessel within a human pelvis, said pelvis having two opposing hip points, a groin, and one leg extending from said groin, said method comprising the steps of:
    stabilizing a shaped mass in position over a selected one of said femoral vessels in said human pelvis, said shaped mass being stabilized relative to at least one of said hip points; and
    applying a inward compressive force through said groin by means of a pelvic apron and a groin strap coupled to said shaped mass, said pelvic apron encircling said human pelvis and said groin strap encircling said one leg, said compressive force directed in a direction through said groin to the posterior portion of said human pelvis, said inward compressive force being generated by a posterior and upward pull by said pelvic apron in combination with a posterior and downward pull by said groin strap, so that said inward compressive force is applied to said shaped mass and ultimately to said underlying femoral vessel.

18. The method of claim 17 where in said step of stabilizing said shaped mass in position, said shaped mass is positioned over said femoral vessel by attachment to a pelvic apron, said pelvic apron being positioned in turn over said human pelvis by means of a hip strap, said hip strap encircling said human pelvis and lying over said opposing points.

19. The method of claim 18 where in said step of applying said compressive force to said pelvic apron, said compressive force is applied to said pelvic apron by means of an extensible elastic groin strap attached at one end to said pelvic apron by means of an extensible elastic groin strap attached at one end to said pelvic apron, extended over said shaped mass, led through said groin, behind said corresponding leg and attached at its opposing end to said pelvic apron in overlapping proximity of said shaped mass.

20. The method of claim 17 where in step of applying said compressive force to said pelvic apron, said compressive force is applied to said pelvic apron by means of an extensible elastic groin strap attached at one end to said pelvic apron, extended over said shaped mass, led through said groin, behind said corresponding leg and attached at its opposing end to said pelvic apron in overlapping proximity of said shaped mass.

21. An apparatus for applying inward pressure to a puncture site in the inguinal region of a human body to stanch blood flow comprising:
    a pellet means for concentrating pressure on said puncture site of said human body;
    a pelvic apron means for positioning said pellet means over said puncture site, said pellet means attached to said pelvic apron means; and
    a separable and adjustable groin strap means connected to said pelvic apron means to apply a compressive force to said pellet means, so that a substantial inward force is adjustably applied to said puncture site and blood flow therefrom is stanched, said groin strap means extending over said point of attachment of said pellet means to said pelvic apron means toward said groin, around and behind said one leg and attaching to said pelvic apron means in the overlapping proximity of said point of attachment thereto of said pellet means to include said pellet means within the encirclement of said groin strap means, said pelvic apron means and groin strap means thus connected with each other to topologically form a figure-of-eight shape having two loops and a crossing point between said two loops, one loop of said figure-of-eight for encircling the trunk of said human body, the other loop of said figure-of-eight shape for encircling a leg of said human body, and said crossing point of said figure-of-eight being positioned substantially over said puncture site a portion of one loop, said crossing point and the contiguous portion of said opposing loop of said figure-of-eight forming a generally straight and generally vertical segment over said pellet means when said apparatus is disposed onto said human body.

* * * * *